United States Patent [19]

Nebe

[11] 4,009,040
[45] Feb. 22, 1977

[54] HEXAARYLBIIMIDAZOLE POLYMERS

[75] Inventor: William John Nebe, Wilmington, Del.

[73] Assignee: E. I. Du Pont de Nemours and Company, Wilmington, Del.

[22] Filed: May 21, 1975

[21] Appl. No.: 579,601

Related U.S. Application Data

[63] Continuation-in-part of Ser. No. 480,408, June 18, 1974, abandoned.

[52] U.S. Cl. ............... 96/115 R; 204/159.23; 260/47 R
[51] Int. Cl.$^2$ .............. G03C 1/68; C08F 2/46
[58] Field of Search ........ 96/115 R; 260/309, 47 R, 260/2.5 N, 88.3 R, 80.72, 79; 526/258

[56] References Cited

UNITED STATES PATENTS

| | | | |
|---|---|---|---|
| 3,597,343 | 8/1971 | Delzenne et al. | 260/88.3 R |
| 3,615,567 | 10/1971 | Wilson | 96/115 R |
| 3,784,557 | 1/1974 | Cescon | 260/309 |
| 3,799,915 | 3/1974 | Dunnovent | 260/80.72 |

FOREIGN PATENTS OR APPLICATIONS 1,168,182  10/1969  United Kingdom ............ 96/115 R

*Primary Examiner*—Joseph L. Schofer
*Assistant Examiner*—Peter F. Kulkosky
*Attorney, Agent, or Firm*—A. P. Mentis

[57] ABSTRACT

Polymers containing hexaarylbiimidazole groups depolymerize upon being struck by radiation and are useful in producing positive images. Exemplary is poly[1,10-bis-4'-[5''(2-o-chlorophenyl-4''-phenyl)imidazolyl]-phenoxydecane].

18 Claims, No Drawings

HEXAARYLBIIMIDAZOLE POLYMERS

RELATED APPLICATION

This application is a continuation-in-part of my copending application Ser. No. 480,408 filed June 18, 1974, now abandoned.

BACKGROUND OF THE INVENTION

1. Field of the Invention

This invention concerns a new class of polymers which depolymerize upon exposure to radiation. They are useful in making direct positive images and are adapted to the formation of negative images as well.

2. Prior Art

U.S. Pat. Nos. 3,445,234; 3,479,185; and 3,784,557 describe the preparation of hexaarylbiimidazoles and their dissociation in the presence of actinic radiation to 2,4,5-triarylimidazoyl free radicals. The hexaarylbiimidazoles together with an electron donor agent comprise a free radical generating system useful for the photopolymerization of ethylenically unsaturated compounds in photopolymerizable compositions. U.S. Pat. No. 3,445,234 describes image-forming radiation-sensitive compositions which contain a leuco dye and a hexaarylbiimidazole (2,4,5-triarylimidazolyl dimer). No art appears to be known which describes hexaarylbiimidazole-containing polymers or their use in forming images by radiation-induced depolymerization.

DESCRIPTION OF THE INVENTION

The present invention comprises a film forming polymer containing a plurality of hexaarylbiimidazole (HABI) groups of the formula

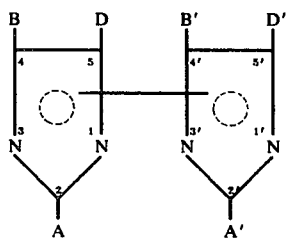

incorporated in the main chain or a cross-linking side chain of the polymer through one A, B or D group and through one A', B' or D' group wherein A, B, D, A', B' and D' individually are aryl groups of 6–12 ring atoms substituted with up to one or more of fluorine, chlorine, bromine, cyano, nitro, phenylthio, or alkyl, alkoxy, acyloxy, acylamido, alkylthio or dialkylsulfamoyl group each having 1–6 carbon atoms. The substituents do not interfere with the dissociation of the hexaarylbiimidazole group to 2,4,5-triarylimidazolyl radicals upon radiation. Each dotted circle in the formula above represents four delocalized electrons, i.e. two conjugated double bonds, which satisfy the valences of the carbon and nitrogen atoms in the imidazole ring.

The aforementioned aryl groups include phenyl, biphenyl, naphthyl, pyridyl, furyl, thienyl, isoquinolyl, indolyl, 1,4-diazaphenyl and the like.

Exemplary are A and A' each being phenyl with an ortho substituent comprising chlorine, fluorine, bromine, methyl or methoxy, and the B, B', D and D' groups each being phenyl or phenyl substituted with alkoxy. Representative examples of substituted aryl groups include

| | |
|---|---|
| o-chlorophenyl | 2,4-xylyl |
| o-bromophenyl | p-acetoxyphenyl |
| p-fluorophenyl | p-acetamidophenyl |
| p-cyanophenyl | p-N,N-dimethylsulfamoylphenyl |
| 2,4-dimethoxyphenyl | 1-naphthyl |
| o-ethoxyphenyl | 4-biphenylyl |
| 2,4-dichlorophenyl | 2-ethyl-1-naphthyl |
| o-hexoxyphenyl | 2-pyridyl |
| o-hexylphenyl | 2-furyl |
| p-tolyl | 3-thienyl |
| m-tolyl | 1-isoquinolyl |
| o-nitrophenyl | 2-indolyl |
| p-methylthiophenyl | 2-(1,4-diazaphenyl) |
| 2,4,6-trimethylphenyl | 3,4-methylenedioxyphenyl |
| p-phenylthiophenyl | p-nitrophenyl |

The HABI groups occur in the main chain of the polymer or in cross-linking side chains. The number of such HABI groups can vary over a wide range depending on the nature and molecular weight of the polymer but generally contain at least 5 such groups. A low molecular weight linear polymer may contain fewer groups than a high molecular weight polymer containing a large number of cross-linking groups. The guiding consideration is that the polymer should contain a sufficient number of HABI groups so that the polymer, when struck by radiation, is split into a significant number of smaller molecular weight fragments by dissociation of the hexaarylbiimidazole groups. Preferred are polymers which contain 5–200 HABI groups.

The hexaarylbiimidazole groups are joined to the polymer chain through bonding with carbon atoms of two of the aryl groups of the HABI unit. It is preferred that the HABI groups are attached to the polymer chain through bonds arising from a complementary pair of aryl groups in the molecule, i.e., 2,2', 4,4', or 5,5', because of the ease in making such polymers.

The invention comprises any polymer in which HABI groups can be incorporated. Such polymers may be linear, branched or three-dimensional. Preferred are polymers which contain the repeating unit

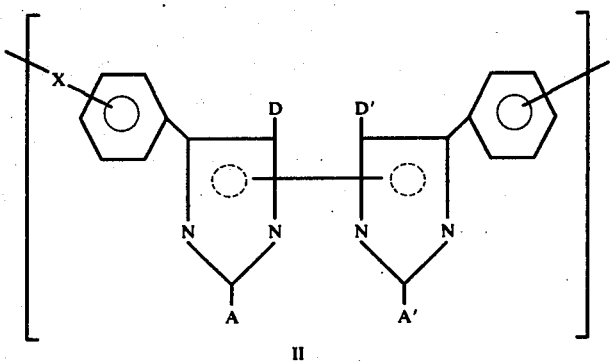

II wherein X is a divalent radical derived by removal of two hydrogen atoms from any difunctional compound useful for the preparation of a low (~1000) to high (~100,000) molecular weight polymer. The difunctional compound is useful for the preparation of condensation polymers including polyesters, polythiolesters, polyamides, polythioamides, polyimides, polythioimides, polyurethanes, polythiourethanes, polyureas, polythioureas, polyethers, polythioethers, polyamines, polyacetals and silicones. Representative examples of difunctional compounds include diacids, dialcohols, diamines, diamides, diisocyanates, diphenols, dibromides, dichlorides, and the like. Representative examples of difunctional compounds include:

| | |
|---|---|
| adipic acid | 1,10-decanediol |
| sebacic acid | 1,4-cyclohexanediol |
| succinic acid | 2,2-bis(4-hydroxyphenyl)- |
| glutaric acid | propane |
| β-methylglutaric acid | hexamethylenediamine |
| suberic acid | p-phenylenediamine |
| dodecanedioc acid | tetramethylenediamine |
| cyclopentane-1,1-diacetic acid | N,N'-dimethylethylenediamine |
| β-phenyladipic acid | 1,4-diaminocyclohexane |
| biphenyl-4,4'-dicarboxylic acid | m-xylylenediamine |
| ethylene glycol | p,p'-diaminodicyclohexyl- |
| 1,4-butanediol | methane |
| 1,6-hexanediol | toluene diisocyanate |
| 1,3-propanediol | hexamethylene diisocyanate |

-continued p-phenylene diisocyanate
p,p'-dicyclohexylmethane diisocyanate
ethylene dibromide
1,6-dichlorohexane
ω,ω'-dibromo-p-xylene
ω,ω'-dichloro-p-xylene Representative examples of divalent X radicals include:

| | m equals |
|---|---|
| $-O(CH_2O)_m-$ | 5–300; preferably 5–100 |
| $-O(CH_2)_mO-$ | 5–50; preferably 5–12 |
| $-O(CH_2CH_2O)_m-$ | 1–500; preferably 1–150 |
| $-O-\overset{O}{\underset{\|}{C}}(CH_2)_m\overset{O}{\underset{\|}{C}}-O-$ | 2–22; preferably 2–12 |
| $*-O-\overset{O}{\underset{\|}{C}}-N(\overset{R}{\underset{\|}{}})(CH_2)_mN(\overset{R}{\underset{\|}{}})-\overset{O}{\underset{\|}{C}}-O-$ | 2–22; preferably 2–12 |
| $-[\overset{H}{\underset{\|}{N}}-(CH_2)_6-NH-\overset{O}{\underset{\|}{C}}-(CH_2)_4-\overset{O}{\underset{\|}{C}}]_m-$ | 1–100; preferably 1–25 |

*R is H or alkyl of 1 to 3 carbons.

Polymers of structure II are prepared by a reaction scheme in which the last step is polymer-forming and involves the oxidative coupling of a substituted bis-2,4,5-triarylimidazole to form the polymers of the invention. Preparation of hexaarylbiimidazole dimers is described by Cescon in U.S. Pat. No. 3,784,557 and by Hayashi et al., Bull. Chem. Soc. Japan, 33, 565 (1960), and Cescon and Dessauer, U.S. Pat. No. 3,445,234. The preferred method of preparation generally yields the 1,2'-hexaarylbiimidazoles, although other isomers such as the 1,1'-, 1,4'-, 2,2'-, 2,4'-, and 4,4'-hexaarylbiimidazoles are also obtained. For the purpose of this invention, it is immaterial which isomer is employed.

In the following reaction scheme, Z is preferably Cl or Br.

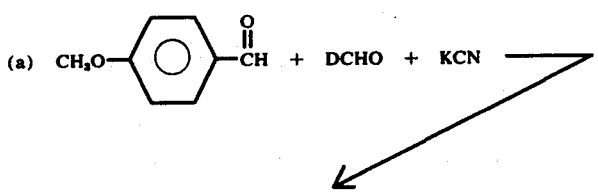

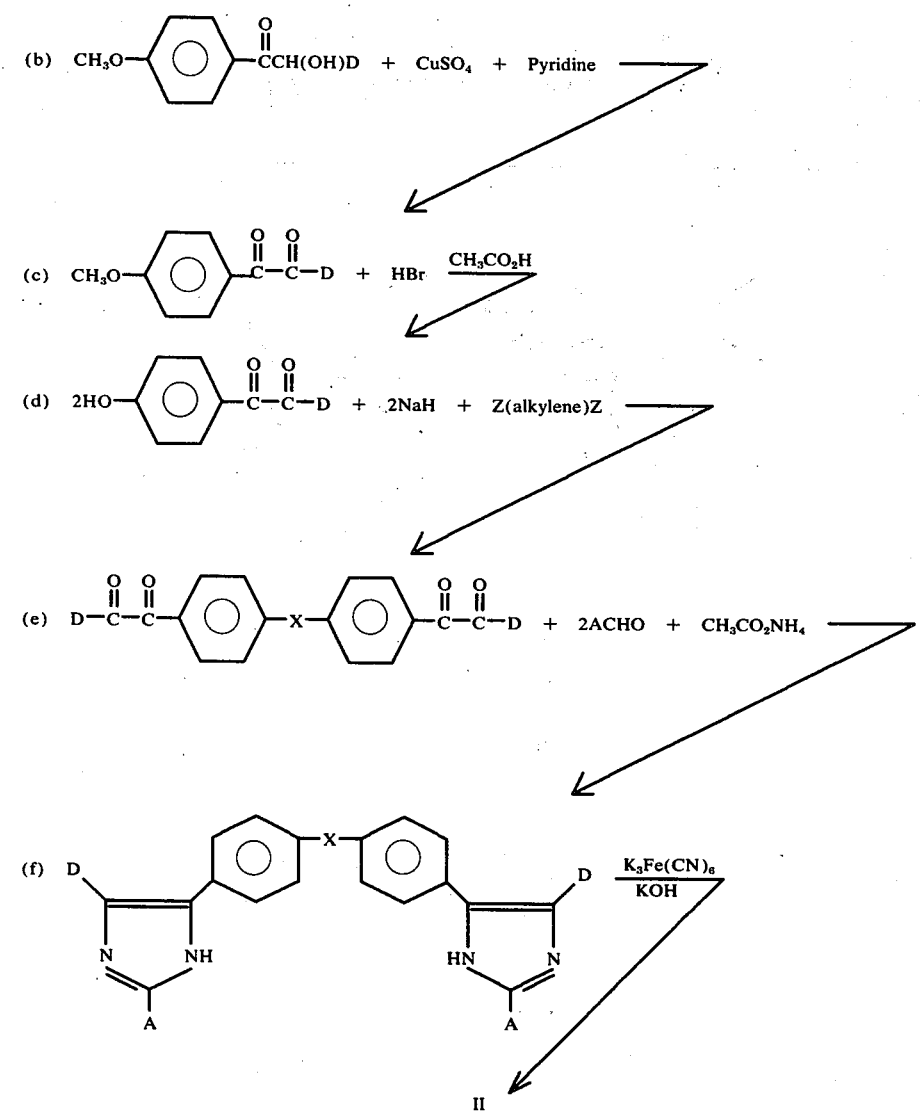

Other polymer structures may be prepared by use of modified preparative schemes. For example, polymer A below wherein X is a polyurethane, can be prepared by reaction of 4-hydroxybenzil with urethane prepolymer, prepared from HO[(CH$_2$)$_4$O]$_3$H with p,p'-diaminodicyclohexylmethane diisocyanate, to obtain the intermediate benzil. Reaction with o-chlorobenzaldehyde and ammonium acetate gives the intermediate triarylimidazole. Oxidative coupling with potassium ferricyanide in alkali gives the desired hexaarylbiimidazole polymer A.

A.

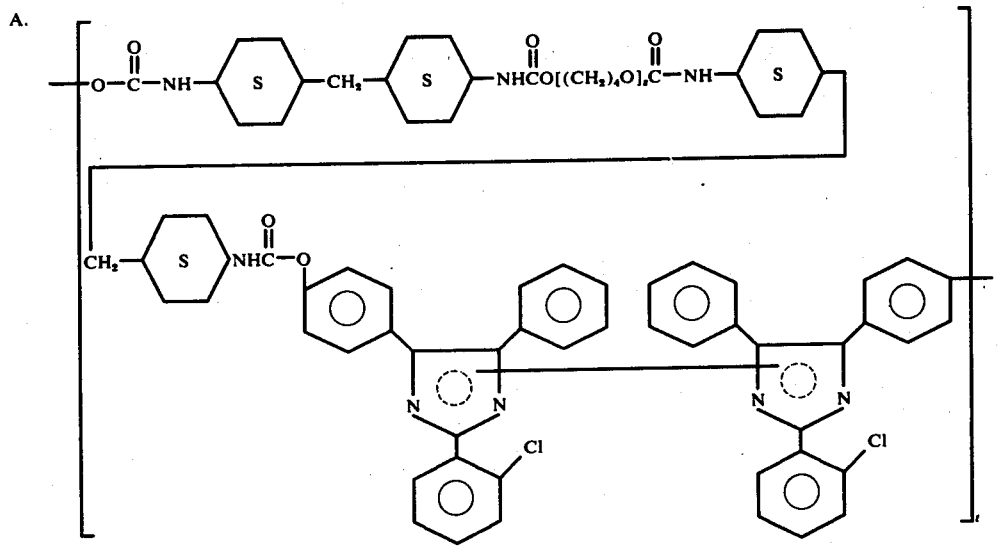

where
s = 5–100, preferably 5–20 and
t = 5–50, preferably 5–20.

where $s = 5$–100, preferably 5–20 and $t = 5$–50, preferably 5–20.

Polymer B wherein X contains a hydrocarbon polymer backbone is prepared by reaction of 4-hydroxybenzil with a copolymer of styrene and p-bromomethylstyrene to give the intermediate benzil. Reaction of this benzil with o-chlorobenzaldehyde and ammonium acetate followed by oxidative coupling of the triarylimidazole obtained gives the desired hexaarylbiimidazole polymer B.

B.

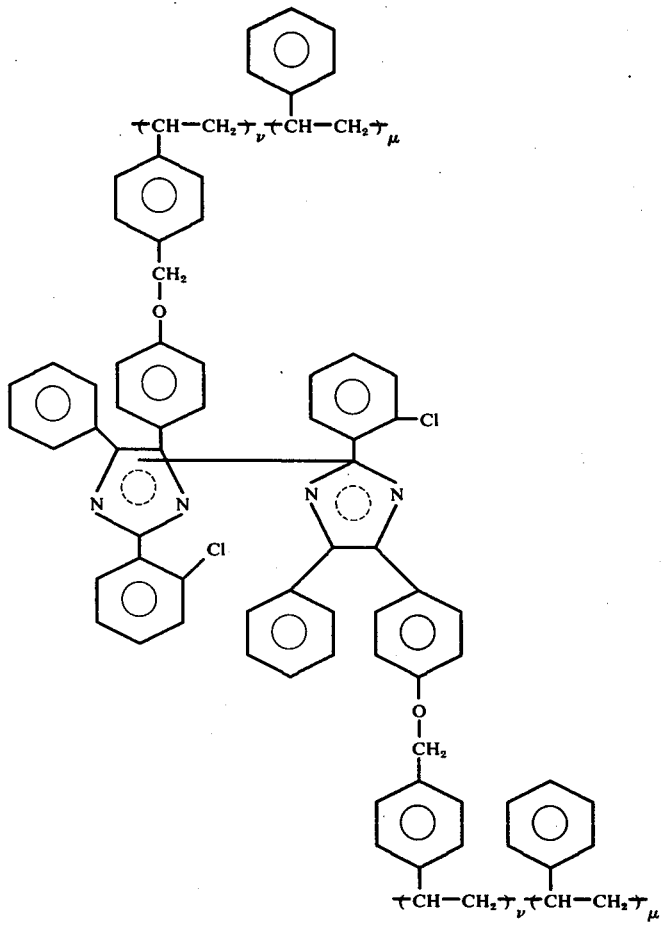

μ = 100 to 10000, preferably 50–200
ν = 1 to 100, preferably 1 to 2.

Polymer C in which the 2,2'-aryl rings of the hexaarylbiimidazole group are linked to the polymer chain can be prepared by reaction of the dibromide of HO(CH$_2$CH$_2$O)$_j$H with the sodium salt of 2-chloro-4-hydroxybenzaldehyde diethylacetal followed by mild acid hydrolysis to give the intermediate aldehyde,

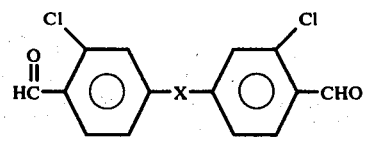

where X = —O(CH$_2$CH$_2$O)$_j$—.

Reaction of this bis(aldehyde) with benzil and ammonium acetate followed by oxidative coupling of the bis(triarylimidazole) obtained gives the desired hexaarylbiimidazole polymer C.

C.

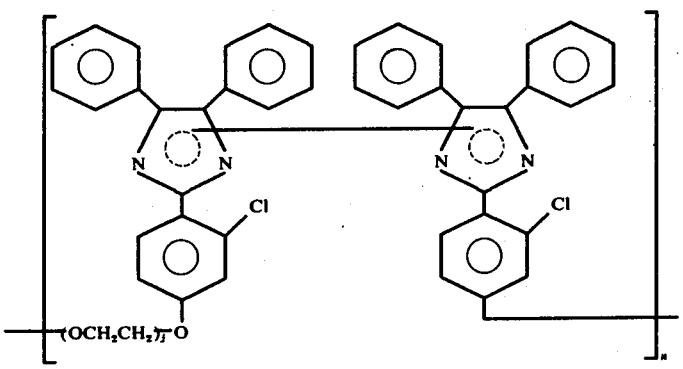

j = 1-500, preferably 1-150;
n = 5-50, preferably 5-20.

Polymer D which incorporates the hexaarylbimidazole groups into the polymer by linking through the 2,2'-aryl rings is prepared by reaction of 2-chloro-4-hydroxybenzaldehyde with hexamethylenediisocyanate to give the intermediate aldehyde,

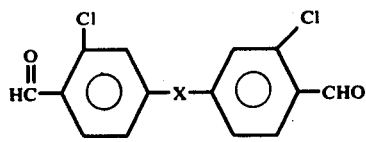

where

Reaction of this bis(aldehyde) with benzil and ammonium acetate followed by oxidative coupling of the bis(triarylimidazole) obtained gives the desired hexaarylbiimidazole polymer D.

D.

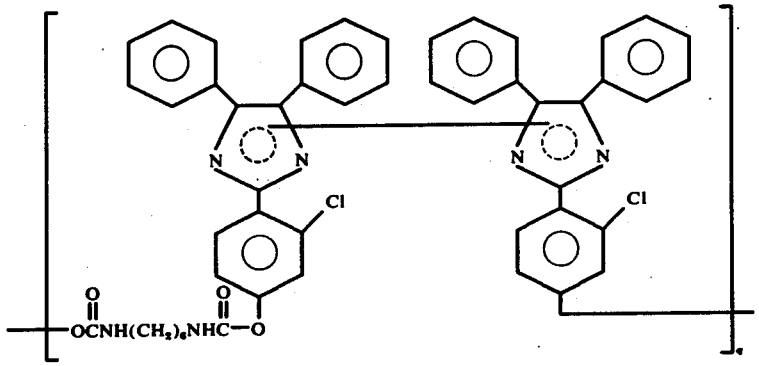

q = 5-50, preferably 5-20.

The hexaarylbiimidazole polymers are useful for the preparation of relief images. In this process an article comprising a layer of a photosensitive polymer of this invention generally as a film of a thickness of 0.01 to 25 mils (0.0000254 to 0.0635 cm) on an inert substrate is imagewise exposed to radiation of wavelength 2000A to 8000A, preferably 2000-4200A and most preferably 2500-4200A for a time sufficient to effect substantial cleavage of the polymer. The exposed article is then developed by a conventional method such as wash out, thermal development, toning and the like.

Cleavage of the polymer during exposure to radiation occurs by dissociation of the hexaarylbiimidazole groups to form the corresponding 2,4,5-triarylimidazolyl radicals in the areas struck by the radiation. Thus the cleaved polymer fragments are readily removed by solvent washout to leave a positive image in the areas not struck by radiation. It is characteristic of the polymers that approximately one quantum of radiation will rupture one hexaarylbiimidazole group, and hence photosensitive compositions containing these polymers are relatively fast. The polymers are relatively insensitive to atmospheric oxygen.

The hexaarylbiimidazole polymers are particularly suitable for the formation of direct positive images. Preferably, the polymer is dissolved in a suitable solvent, with or without a reducing agent, and the solution is used to apply a film of the material onto a suitable substrate following known techniques. Preferred solvents include chlorinated hydrocarbons, especially methylene chloride. By "substrate" is meant any natural or synthetic support which is capable of existing in film or sheet form and can be flexible or rigid. For example, the substrate can be a metal sheet or foil, a sheet of film of synthetic organic resin, cellulose paper, fiberboard and the like, or a composite of two or more of these materials. Many specific substrates are known in the art.

The photosensitive compositions may optionally contain other materials inert to the photodegradation reaction. Such materials include thermoplastic and non-thermoplastic binders useful for varying the physical properties of the resultant polymeric images. In addition, plasticizers may be added to lower the glass transition temperature and facilitate selective development. If desired the polymers may also contain immiscible polymeric or nonpolymeric organic or inorganic fillers or reinforcing agents which are essentially transparent, e.g., the organophilic silicas, bentonites, silica, powdered glass, colloidal carbon, as well as various types of dyes and pigments. Other useful additives which may be employed include sensitizers to improve the efficiency of the radiation and adhesion promoters.

The photosensitive compositions are used with or without a free-radical producing electron donor agent, such as leuco crystal violet, tris(4-diethylamino-2-methylphenyl)methane, or substituted 2-mercaptobenzoxozoles, which are preferred. Such sensitizers as Michler's ketone may be added. Various energy transfer dyes such as Rose Bengal and Eosin Y can also be used.

Imagewise exposure is conveniently carried out by exposing a layer of the photosensitive composition to actinic radiation through a process transparency, i.e., an image-bearing transparency, consisting solely of areas substantially opaque and substantially transparent to the radiation being used where the opaque areas are substantially of the same optical density; for example, a so-called line of halftone negative or positive. Process transparencies may be constructed of any suitable materials including cellulose acetate film and polyester film. After exposure, the depolymerized material is preferably removed by solvent washout to leave polymer under the opaque areas of the process transparency, i.e., the areas not struck by radiation passing through the transparency. Thus, a "reverse image" is obtained, and hence the system is "positive working."

Suitable sources of radiation for use in imaging with the hexaarylbiimidazole polymers, in addition to sunlight, include carbon arcs, mercury vapor arcs, fluorescent lamps with ultraviolet radiation-emitting phosphors, electronic flash units, and photographic flood lamps.

When artificial radiation sources are used, the distance between the photosensitive layer and the radiation source may be varied according to the radiation sensitivity of the copolymer. Customarily, mercury-vapor arcs are used at a distance of 1.5 to 20 inches from the photosensitive layer.

The length of time for which the compositions are exposed to radiation may vary upwards from a few seconds. Exposure times will vary, in part, according to the nature of the hexaarylbiimidazole polymer, the number and types of substituent groups, and the type of radiation.

Uses for the photosensitive compositions of the present invention will be evident to those skilled in the art. For example, when coated on metal surfaces, they are useful for making presensitized lithographic and gravure printing plates. Use of a grained aluminum base in combination with a photodepolymerizable polymer coating results in a developed lithographic plate. The plate is first coated with water and is then contacted with a roller which wets only the polymer image with ink. The inked plate can then be used in lithographic printing in the usual way.

Specific Embodiments of the Invention

In the following all parts are by weight and all temperatures are Centigrade unless stated otherwise. Example 1 is a typical, general procedure which illustrates the preparation of a suitable polymer of this invention. By choice of appropriately substituted starting materials other polymers of the invention may be similarly prepared.

EXAMPLE 1

Preparation of 4-Methoxybenzoin (1)

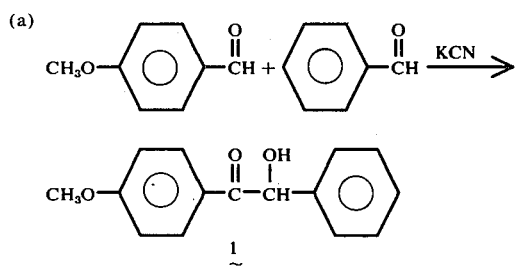

A solution of 178.6 g (1.3 mole) of 4-methoxybenzaldehyde and 139.0 g (1.3 mole) of benzaldehyde in 460 ml of 95% ethanol and 210 ml of water containing 32.8 g of potassium cyanide was prepared and heated to reflux for 1.5 hours. The solution was then steam-distilled until no further organic material distilled. The residual paste was crystallized from ethanol to give 180 g (58%) of 4-methoxybenzoin, mp, 105°–106°, lit., 106°.

Preparation of 4-Methoxybenzil (2)

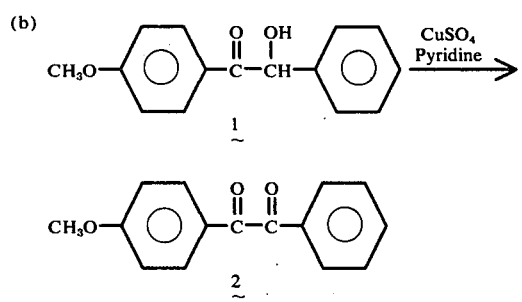

A mixture of 463 g of copper sulfate, 450 g of pyridine, and 180 g of water was stirred and heated to 85° for 10 hours. A 218-g sample (1.1 mole) of 4-methoxybenzoin was added and the heating and stirring continued for 2 hours at 85°. After the solution had cooled, 490 ml of concentrated hydrochloric acid was added and the resulting solid filtered. The solid and filtrate were washed with ether, and the ether layer was washed with water and dried. The ether was distilled, giving a brown solid that was chromatographed on a neutral alumina column. The product was eluted with carbon tetrachloride and crystallized in carbon tetrachloride; yeild 150 g (68%) of 4-methoxybenzil; mp 56°–58°, lit., 58°.

c. Preparation of 4-Hydroxybenzil (3)

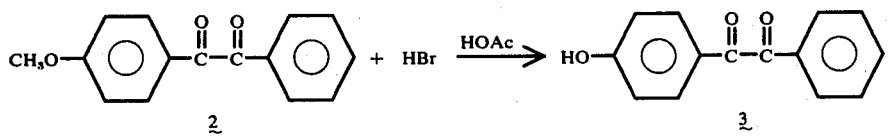

A solution of 50 g (0.21 mole) of 4-methoxybenzil in 250 ml of acetic acid and 300 ml of 48% hydrobromic acid was heated to reflux for 10 hours. A solid that separated on cooling was recovered by filtration and the filtrate extracted with ether. The solid was dissolved in ether, the ether solutions combined and extracted with 10% potassium hydroxide. The potassium hydroxide solution was washed with ether and neutralized with hydrochloric acid. The resulting solid was dissolved in ether, the solution dried over magnesium sulfate, and the ether removed by distillation. The resulting dark, brown solid was recrystallized from benzene to yield 30 g (64%) of 4-hydroxybenzil; mp, 138°–140°, lit., 129°–130°.

a 30-minute period and the solution was heated at 50° for 1 hour.

The solution was worked up by adding water and extracting the resulting turbid liquid with ether. The ether solution was dried and the ether evaporated. The resulting solid was recrystallized from benzene to yield 2.0 g (35%) of 1,10-bis-4'-benziloxydecane, mp, 106°–111°.

Anal. Calcd. for $C_{38}H_{38}O_6$: C, 77.26; H, 6.48 Found: C, 76.13; H, 6.53 C, 76.04; H, 6.55.

e. Preparation of 1,10-Bis-4'-[5''(2''-o-chlorophenyl-4''-phenyl)imidazolyl]phenoxydecane (5)

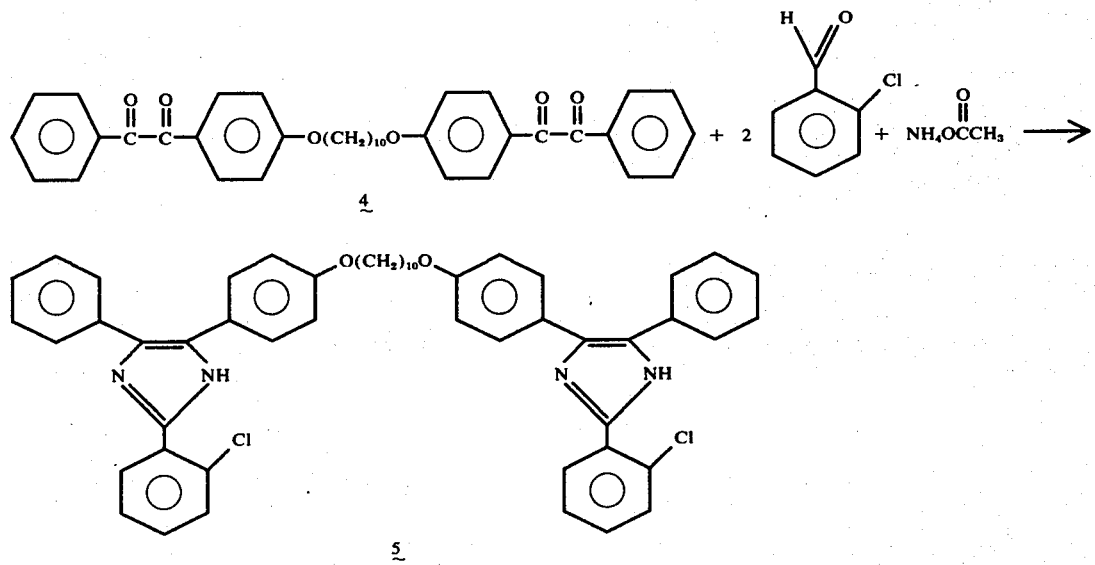

d. Preparation of 1,10-Bis-4'-benziloxydecane (4)

A solution of 1.0 g (0.0017 mole) of 1,10-bis-4'-benziloxydecane, 0.44 g (0.0034 mole) of o-chloroben-

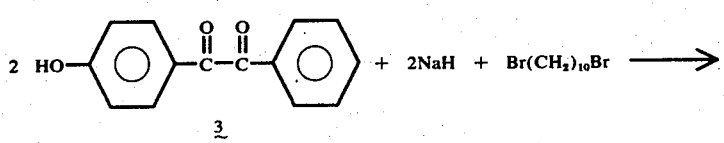

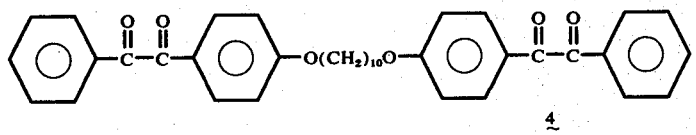

A solution of 4.5 g (0.01 mole) of 4-hydroxybenzil in 150 ml of dimethylformamide (DMF) was stirred and treated, in portionwise addition, with 0.82 g (0.01 mole) of sodium hydride (58% in mineral oil) over a 30-minute period. A 3.0-g sample (0.005 mole) of 1,10-dibromodecane in 50 ml of DMF was added over zaldehyde and 0.8 g of ammonium acetate (0.0136 mole) in 30 ml of acetic acid was heated to reflux for 2 hours. The reaction mixture was cooled, diluted with water and extracted with ether. The ether extracts were combined, dried and the ether evaporated to leave a paste that was chromatographed on neutral alumina to yield 0.42 g (30%) of 1,10-bis-4'-[5"(2"-o-chlorophenyl-4"-phenyl)imidazolyl]phenoxydecane as a white solid, mp, 66–71°. The product could not be recrystallized.

Anal. Calcd. for $C_{52}H_{48}Cl_2N_4O_2$: C, 75.08; H, 5.82; N, 6.73 Found: C, 74.24; H, 5.58; N, 6.08. C, 74.04; H, 5.77; N, 6.50.

f. Preparation of Poly-1,10-bis-4'-[5"(4"-o-chlorophenyl-4"-phenyl)imidazolyl]phenoxydecane (6) ("Poly-HABI")

EXAMPLE A

Exposure of Poly-HABI in a Positive System

A solution of 0.5 g of "poly-HABI" (6) and 0.1 g of 5-tert-butyl-2-mercaptobenzoxazole in 10 ml of methylene chloride was coated onto aluminum using a doctor knife set at 5 mil (0.0127 cm). This dilute solution gave a very thin film.

The resultant plate was exposed to radiation from a 100-watt high pressure mercury lamp through an ori-

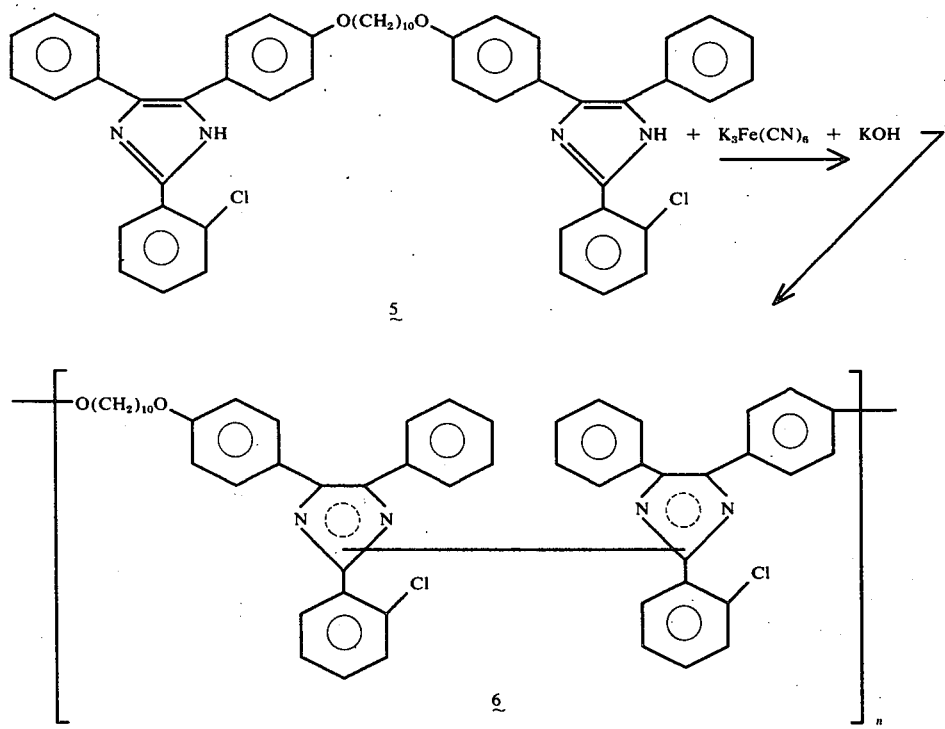

A solution of 5.0 g (0.00602 mole) of 1,10-bis-4'[5'λ'(2"-o-chlorophenyl-4"-phenyl)imidazolyl]phenoxydecane in 100 ml of benzene was mixed with a solution of 12.0 g of potassium ferricyanide and 5.5 g of potassium hydroxide in 75 ml of water. From this point on all procedures were carried out with the exclusion of light. This mixture was then stirred vigorously at room temperature for 18 hours. The liquids were then separated and the benzene layer washed with water and dried over magnesium sulfate. The magnesium sulfate was removed by filtration and the benzene evaporated to give a film-like product, poly-1,10-bis-4'-[5"(2"-o-chlorophenyl-4"-phenyl)imidazolyl]phenoxydecane. The polymer was dissolved in methylene chloride and a film cast. The polymer was light yellow in color and had an inherent viscosity of 0.237 (as measured in 0.10% concentration in methylene chloride). An osmotic pressure molecular weight determination gave a minimum value of 10,000–13,000.

Anal. Calcd. for $C_{52}H_{46}Cl_2N_4O_2$: C, 75.08; H, 5.82; N, 6.73 Found: C, 73.46; H, 6.43; N, 5.70. C, 73.38; H, 6.42; N, 5.71.

The oxidation of step (f) may also be accomplished by agitating a benzene or chloroform solution of the imidazole (5) with lead dioxide ($PbO_2$).

ented polyester process transparency. The photodegraded polymer was washed out with carbon tetrachloride to leave a positive image in the areas not struck by radiation.

| Exposure Time | Results (Positive Image) |
|---|---|
| 3 minutes | Strong image |
| 2 minutes | " |
| 1 minute | " |
| 30 seconds | " |
| 15 seconds | " |
| 10 seconds | Image |
| 5 seconds | Weak Image |

EXAMPLE B

Exposure of Poly-HABI in a Positive System

A solution of 0.5 g of "poly-HABI" (6) and 0.1 g of 5-tert-butyl-2-mercaptobenzoxazole in 3 ml of methylene chloride was coated onto an aluminum plate with a doctor knife set at 5 mil (0.0127 cm).

The resultant plate was exposed to radiation from a 100-watt high pressure mercury lamp for 3 minutes, the photodegraded polymer was washed out to leave a positive image with noticeable relief (image thickness).

EXAMPLE C

Exposure of "Poly-HABI" in a Positive System Without a Reducing Agent

A solution of 0.5 g of "poly-HABI" (6) in 10 ml of methylene chloride was cast onto an aluminum plate from a doctor knife set at 5 mils (0.0127 cm) (no reducing agent was used).

The resultant plate was exposed to radiation from a 100-watt high pressure mercury lamp. This gave a blue image which could be washed out to a positive image. If the plate was not washed out the blue color faded, but a new image could be obtained by a second exposure. This experiment demonstrates the photochromic nature of this polymer.

An additional utility lies in employing the polymers of the invention as photoinitiators in photopolymerizable systems containing a monomer or monomers, binder and other constituents normally employed in such systems, as described, for example, in U.S. Pat. No. 3,479,185 to Chambers. When used as a photoinitiator, the concentration of the polymer employed is generally 0.5–10% by weight based on the total polymerizable composition. The following example illustrates this additional use.

EXAMPLE D

| "Poly-HABI" as an Initiator in Photopolymerization | |
|---|---|
| A solution comprising: | |
| "Poly-HABI" (6) | 0.4 g |
| 5-tert-butyl-2-mercaptobenzoxazole | 0.05 g |
| Elvacite 2041 polymethyl methacrylate[1] | 1.0 g |
| Elvacite 2008 polymethyl methacrylate[2] | 1.4 g |
| 1,1,1-Tris(methacryloxymethyl)propane | 1.0 g |
| Bis(2-acryloxyethyl)ether | 0.7 g |

[1]Low molecular weight polymethyl methacrylate of E. I. du Pont de Nemours and Company
[2]High molecular weight polymethyl methacrylate in 20 ml of methylene chloride was cast onto an aluminum plate with a doctor knife set at 8 mils (0.0204 cm). This was overcoated with 2% polyvinyl alcohol in water.

The plate was exposed to radiation from a commercial nuArc light source for 1, 2, and 3-minute periods to form a negative image which was developed by successive washout with water and methyl chloroform.

I claim:

1. A film forming polymer containing a plurality of hexaarylbiimidazole groups of the formula

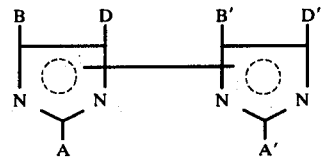

incorporated in the main chain or a cross-linking side chain of the polymer through one A, B or D group and through one A', B' or D' group wherein A, B, D, A', B' and D' individually are aryl groups of 6–12 ring atoms substituted with up to one or more of fluorine, chlorine, bromine, cyano, nitro, phenylthio, or alkyl, alkoxy, acyloxy, acylamido, alkylthio or dialkylsulfamoyl group each having 1–6 carbon atoms.

2. A polymer of claim 1 in which all the said aryl groups are each phenyl.

3. A polymer of claim 1 containing at least 5 of said hexaarylbiimidazole groups.

4. A polymer of claim 1 containing 5 to 200 of said hexaarylbiimidazole groups.

5. A polymer of claim 1 having a repeating unit of the formula

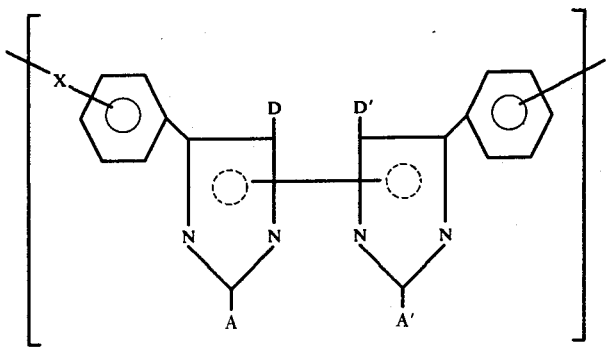

wherein X is a divalent radical.

6. A polymer of claim 5 where X is

wherein $m$ is 5–50.

7. A polymer of claim 6 wherein $m$ is 5–12.

8. A polymer of claim 7 where $m$ is 10.

9. A polymer of claim 5 in which A and A' each are o-chlorophenyl.

10. A polymer of claim 5 wherein the polymer is poly-1,10-bis-4'-[5''(2''-o-chlorophenyl-4''-phenyl)imidazolyl]-phenoxydecane.

11. A photodepolymerizable composition for producing an image comprising a polymer of claim 1.

12. A photodepolymerizable composition for producing an image comprising a polymer of claim 5.

13. A photodepolymerizable composition for producing an image comprising the polymer of claim 9.

14. The process of producing an image comprising the step of imagewise exposing a composition of claim 11 to actinic radiation.

15. The process of producing an image comprising the step of imagewise exposing the composition of claim 12 to actinic radiation.

16. The process of producing an image comprising the step of imagewise exposing the composition of claim 13 to actinic radiation.

17. The process of using a polymer of claim 1 as an initiator of photopolymerization.

18. The process of claim 17 where the polymer is poly-1,10-bis-4'-[5''(2''-o-chlorophenyl-4''-phenyl)-imidazolyl]phenoxydecane.

* * * * *